United States Patent [19]

Schoen et al.

[11] Patent Number: 5,635,511
[45] Date of Patent: Jun. 3, 1997

[54] TREATMENT OF HEART RHYTHM DISORDERS BY ADMINISTRATION OF 3-PHENYLSULFONYL-3,7-DIAZABICYCLO[3.3.1]NONANE COMPOUNDS.

[75] Inventors: Uwe Schoen, Burgdorf; Arman Farjam, Moenchengladbach; Reinhard Brueckner, Hanover; Dieter Ziegler, Hemmingen, all of Germany

[73] Assignee: Kali-Chemie Pharma GmbH, Hanover, Germany

[21] Appl. No.: 594,946

[22] Filed: Jan. 31, 1996

Related U.S. Application Data

[62] Division of Ser. No. 382,262, Feb. 1, 1995, Pat. No. 5,576,327.

[30] Foreign Application Priority Data

Feb. 1, 1994 [DE] Germany .................. 44 02 931.4

[51] Int. Cl.$^6$ .................. A61K 31/44; C07D 471/08
[52] U.S. Cl. .................. 514/278; 514/300; 546/18; 546/112; 546/114; 546/122
[58] Field of Search .................. 546/112, 18, 114, 546/122; 514/300, 278

[56] References Cited

U.S. PATENT DOCUMENTS

| 4,906,640 | 3/1990 | Schoen et al. | 546/122 |
|---|---|---|---|
| 4,983,611 | 1/1991 | Schoen et al. | 514/300 |
| 5,153,214 | 10/1992 | Bhagwat et al. | 514/381 |

FOREIGN PATENT DOCUMENTS

WO91/07405  5/1991  WIPO .

OTHER PUBLICATIONS

Chemical abstracts, vol. 113, No. 13, 1990, Abstract No. 115277q.

*Primary Examiner*—Frederick Krass
*Attorney, Agent, or Firm*—Evenson, McKeown, Edwards & Lenahan P.L.L.C.

[57] ABSTRACT

The use of 3,7,9,9-tetrasubstituted 3-phenylsulfonyl-3,7-diazabicyclo[3.3.1]nonane compounds for treating cardiac arrhytmias in larger mammals, including humans; novel antiarrhythmically active 3,7,9,9-tetrasubstituted compounds corresponding to the general formula Ia

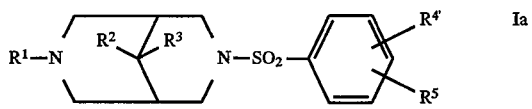

in which $R^1$ is an alkyl group having 1–6 carbon atoms or a cycloalkylalkyl group having 4–7 carbon atoms,
$R^2$ is lower alkyl, and
$R^3$ is lower alkyl, or
$R^2$ and $R^3$ together form an alkylene chain having 3–6 carbon atoms,
$R^{4'}$ is cyano, an $R^6$—O—CO— group in which $R^6$ is lower alkyl, an $R^7$—SO$_2$—NH— group in which $R^7$ is lower alkyl, or an $R^8$—CO—NH— group in which $R^8$ is lower alkyl or a phenyl group which is optionally substituted by halogen, cyano, nitro, or an $R^9$—SO$_2$— radical in which $R^9$ is lower alkyl, or an imidazolyl radical located in position 4 of the phenyl ring, and
$R^5$ is hydrogen or halogen, and physiologically acceptable acid addition salts thereof, and processes and intermediates for preparing them.

2 Claims, No Drawings

TREATMENT OF HEART RHYTHM DISORDERS BY ADMINISTRATION OF 3-PHENYLSULFONYL-3,7-DIAZABICYCLO [3.3.1]NONANE COMPOUNDS.

This application is a division of application Ser. No. 08/382,262, filed Feb. 1, 1995, now U.S. Pat. No. 5,576,327.

BACKGROUND OF THE INVENTION

The present invention relates to the use of 3,7,9,9-tetrasubstituted 3,7-diazabicyclo[3.3.1]nonane compounds which in the 3-position carry a phenylsulfonyl radical which is substituted in the phenyl ring or of salts thereof as antiarrhythmically active pharmacological agents, to pharmaceutical compositions containing these compounds, and o novel 3,7,9,9-tetrasubstituted 3-phenylsulfonyl-3,7-diazabicyclo[3.3.1]nonane compounds having antiarrhythmic activity, as well as to processes and intermediates for the preparation of these compounds.

Schoen et al., U.S. Pat. No. 4,906,640 discloses 3-sulfonyl-3,7-diazabicyclo[3.3.1]nonane derivatives which exert a stomach motility-regulating effect in the gastrointestinal tract.

SUMMARY OF THE INVENTION

The object of the present invention is to provide a method of treating cardiac arrhythmias using antiarrhythmically active agents and pharmaceutical preparations having an improved activity profile.

Another object of the invention is to provide novel 3,7-diazabicyclo[3.3.1]nonane compounds having useful pharmacological properties.

These and other objects of the invention are achieved by providing a method of treating cardiac arrhythmias in a mammal comprising administering to the mammal an effective cardiac rhythm affecting amount of a 3-phenylsulfonyl-3,7-diazabicyclo[3.3.1]nonane compound corresponding to the formula I

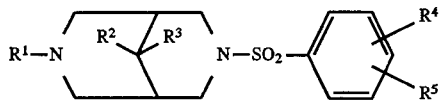

in which $R^1$ is an alkyl group having 1–6 carbon atoms or a cycloalkylalkyl group having 4–7 carbon atoms, $R^2$ and $R^3$ are each independently lower alkyl or together form an alkylene chain having 3–6 carbon atoms, $R^4$ is halogen, nitro, trifluoromethyl or cyano, an $R^6$—O—CO— group in which $R^6$ is lower alkyl, an $R^7$—SO$_2$—NH— group in which $R^7$ is lower alkyl, or an $R^8$—CO—NH— group in which $R^8$ is lower alkyl or a phenyl ring which is optionally substituted by halogen, cyano, nitro or an $R^9$—SO$_2$— radical in which $R^9$ is lower alkyl, or an imidazolyl radical located in the 4-position of the phenyl ring, and $R^5$ is hydrogen or halogen;

or a physiologically acceptable acid addition salt thereof.

The objects in accordance with a further aspect of the invention are achieved by providing a compound corresponding to the formula Ia

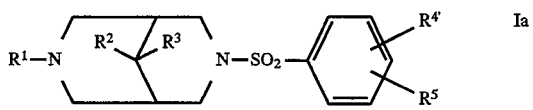

in which $R^1$ is an alkyl group having 1–6 carbon atoms or a cycloalkylalkyl group having 4–7 carbon atoms, $R^2$ and $R^3$ are each independently lower alkyl or together form an alkylene chain having 3–6 carbon atoms, $R^{4'}$ is cyano, an $R^6$—O—CO— group in which $R^6$ is lower alkyl, an $R^7$—SO$_2$—NH— group in which $R^7$ is lower alkyl or an $R^8$—CO—NH— group in which $R^8$ is lower alkyl or a phenyl group which is optionally substituted by halogen, cyano, nitro or an $R^9$—SO$_2$— radical in which $R^9$ is lower alkyl, or an imidazolyl radical located in the 4-position of the phenyl ring, and $R^5$ is hydrogen or halogen;

or a physiologically acceptable acid addition salt thereof.

DETAILED DESCRIPTION OF PREFERRED EMBODIMENTS

It has now been found that a group of 3,7-diazabicyclo [3.3.1]nonane compounds substituted in the 3-position by a substituted phenylsulfonyl radical have useful pharmacological properties for the treatment of cardiac arrhythmias and exhibit an antiarrhythmic activity profile which makes them suitable for treating cardiac arrhythmias, in particular tachycardiac arrhythmias.

According to the invention, the antiarrhythmic agents used for the treatment of cardiac arrhythmias in larger mammals and humans are 3-phenylsulfonyl-3,7-diazabicyclo-[3.3.1]nonane compounds corresponding to the formula I

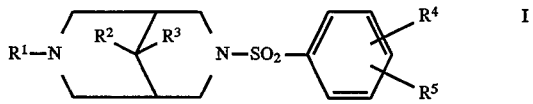

in which $R^1$ is an alkyl group having 1–6 carbon atoms or a cycloalkylalkyl group having 4–7 carbon atoms, $R^2$ is lower alkyl, and $R^3$ is lower alkyl, or $R^2$ and $R^3$ together form an alkylene chain having 3–6 carbon atoms, $R^4$ is halogen, nitro, trifluoromethyl or cyano, an $R^6$—O—CO— group in which $R^6$ is lower alkyl, an $R^7$—SO$_2$—NH— group in which $R^7$ is lower alkyl, or an $R^8$—CO—NH— group in which $R^8$ is lower alkyl or a phenyl group which is optionally substituted by halogen, cyano, nitro or an $R^9$—SO$_2$—radical in which $R^9$ is lower alkyl, or an imidazolyl radical located in the 4-position of the phenyl ring, and $R^5$ is hydrogen or halogen, and their physiologically acceptable acid addition salts.

If $R^1$ in the compounds of formula I is an alkyl group, this can be straight-chain or branched and contain 1 to 6, preferably 3 to 5, in particular 4, carbon atoms. A cycloalkylalkyl group $R^1$ can contain 4 to 9, preferably 4 to 7, carbon atoms. Alkyl radicals having 3 to 5 carbon atoms have proven to be particularly suitable $R^1$ radicals.

If the substituents $R^2$ and $R^3$ are lower alkyl, they may be the same or different and can be straight-chain or branched and contain 1 to 4, preferably 1 to 3, carbon atoms and be, in particular, methyl. If $R^2$ and $R^3$ together form an alkylene group, this can contain 3 to 6, preferably 4 to 5, carbon atoms. Compounds in which $R^2$ and $R^3$ are each lower alkyl, in particular methyl, have proven particularly suitable.

If the substituent $R^4$ contains a lower alkyl group, this can be straight-chain or branched and contain 1 to 4, in particular 1 to 3, carbon atoms and preferably be the methyl group. The substituent $R^4$ is preferably cyano or an imidazolyl radical located in the 4-position of the phenyl ring.

Suitable pharmacologically acceptable acid addition salts of the compounds of formula I include, for example, their salts with inorganic acids, e.g. hydrohalic acids, in particular hydrochloric acid, sulfuric acid or phosphoric acids, or with organic acids, for example lower aliphatic mono- or dicarboxylic acids such as malonic acid, maleic acid, fumaric acid, lactic acid, tartaric acid, acetic acid or citric acid, or with organic sulfonic acids, for example lower alkanesulfonic acids such as methanesulfonic acid or benzenesulfonic acids optionally substituted in the benzene ring by halogen or lower alkyl, such as p-toluenesulfonic acid.

The invention also relates to the use of the compounds of formula I as antiarrhythmically active pharmacological agents for the production of medicaments and antiarrhythmically active medicaments prepared using these agents.

3-Phenylsulfonyl-3,7-diazabicyclo [3.3.1]nonane compounds corresponding to the general formula Ia

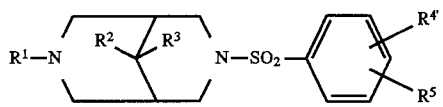

in which
- $R^1$ is an alkyl group having 1–6 carbon atoms or a cycloalkylalkyl group having 4–7 carbon atoms,
- $R^2$ and $R^3$ are each independently lower alkyl or together form an alkylene chain having 3–6 carbon atoms,
- $R^{4'}$ is cyano, an $R^6$—O—CO— group in which $R^6$ is lower alkyl, an $R^7$—SO$_2$—NH— group in which $R^7$ is lower alkyl, or an $R^8$—CO—NH— group in which $R^8$ is lower alkyl or a phenyl group which is optionally substituted by halogen, cyano, nitro or an $R^9$—SO$_2$— radical in which $R^9$ is lower alkyl, or an imidazolyl radical located in the 4-position of the phenyl ring, and
- $R^5$ is hydrogen or halogen, and their physiologically acceptable acid addition salts have not been described previously in the literature and constitute novel, useful active pharmacological compounds which are likewise a part of the present invention.

The other compounds of formula I used as antiarrhythmic agents according to the invention fall within the scope of the compounds described in the aforementioned U.S. Pat. No. 4,906,640 and are disclosed therein.

The 3-phenylsulfonyl-3,7-diazabicyclo[3.3.1]nonane compounds of formula I and their acid addition salts according to the invention are obtained by a process in which, in a known manner:

a) to prepare a compound of the general formula Ie

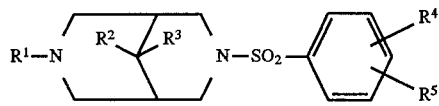

in which $R^1$, $R^2$, $R^3$ and $R^5$ have the above meanings and $R^{4'''}$ is halogen, nitro, trifluoromethyl or cyano, an $R^6$—O—CO— group in which $R^6$ has the above meaning, an $R^7$—SO$_2$—NH— group in which $R^7$ has the above meaning, or an $R^{8'}$—CO—NH— group in which $R^{8'}$ is lower alkyl, a compound corresponding to the general formula II

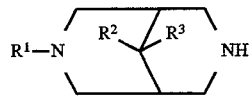

in which $R^1$, $R^2$ and $R^3$ have the above meanings, is reacted with a compound corresponding to formula III

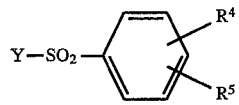

in which $R^{4'''}$ and $R^5$ have the above meanings and Y is a reactive group, or b) to prepare a compound of the general formula Ic

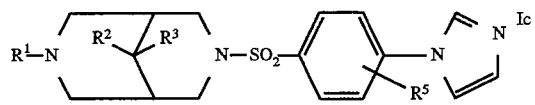

in which $R^1$, $R^2$, $R^3$ and $R^5$ have the above meanings, a compound of the general formula IV

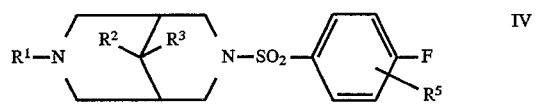

in which $R^1$, $R^2$, $R^3$ and $R^5$ have the above meanings, is reacted with imidazole of the formula V

or c) to prepare a compound of the general formula Id

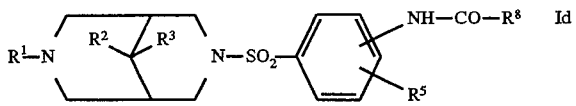

in which $R^1$, $R^2$, $R^3$ and $R^5$ have the above meanings and $R^{8''}$ is a phenyl group which is optionally substituted by halogen, cyano, nitro or an $R^9$—SO$_2$— radical in which $R^9$ is lower alkyl, a compound of the general formula VI

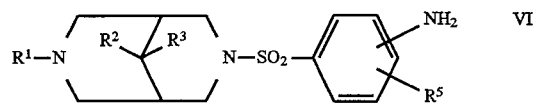

in which $R^1$, $R^2$, $R^3$ and $R^5$ have the above meanings, is acylated using an acid or reactive acid derivative of the general formula VII

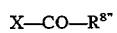

in which $R^{8''}$ has the above meaning and X is hydroxyl or a reactive group, and free compounds of formula I are optionally converted to their acid addition salts or the acid addition salts are converted to the free compounds of formula I.

The reaction of the sulfonic acid derivatives of formula III with the 3,7-diazabicyclo[3.3.1]nonane compounds of formula II according to process variant a) can be carried out by customary methods for sulfonamide formation by acylation. Particularly suitable reactive derivatives include sulfonyl halides, preferably chlorides, and anhydrides of the sulfonic acids of formula IIIb

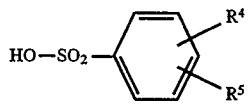   IIIb where $R^{4'''}$ and $R^5$ have the above meanings. Thus, the reactive group Y in the compounds of formula III may be, for example, halogen, in particular chlorine, or a phenylsulfonyloxy group substituted in the phenyl ring by $R^{4'''}$ and $R^5$. The acylation can be carried out in a solvent which is inert under the reaction conditions at temperatures between 0° C. and the boiling point of the solvent. Suitable solvents include halogenated hydrocarbons such as dichloromethane or chloroform, aromatic hydrocarbons such as benzene, toluene or chlorobenzene, cyclic ethers such as tetrahydrofuran or dioxane, dimethylformamide or mixtures of these solvents. If desired, the acylation can be carried out in the presence of an acid-binding agent. Suitable acid-binding agents include inorganic bases, in particular alkali metal carbonates, or organic bases, in particular tertiary lower alkylamines and pyridines, such as e.g. triethylamine or 4-dimethylaminopyridine.

The reaction of compounds of formula IV with imidazole according to process variant b) can be carried out in a known manner in organic solvents which are inert under the reaction conditions at elevated temperatures, for example at temperatures between 70° and 150° C. Particularly suitable solvents include dimethyl sulfoxide, dimethylformamide and acetonitrile. Compounds of formula IV are advantageously reacted with about 3 to 6 equivalents of imidazole. In general, it is advantageous to work with addition of 1–3 equivalents of an inorganic base, for example an alkali metal carbonate.

The reaction of the amino compounds of formula VI with the acids or acid derivatives of formula VII according to process variant c) can be carried out by customary methods for acylation of aniline derivatives. Particularly suitable reactive acid derivatives of formula III include acid halides, preferably chlorides, and acid anhydrides. The reaction of acid derivatives of this type with the compounds of formula VI can be carried out under the customary reaction conditions for amide formation, for example under the reaction conditions described above for process variant a). If acids of formula VII are used, the reaction can advantageously be carried out in the presence of a coupling reagent known from peptide chemistry to be suitable for amide formation. Noteworthy examples of coupling reagents which promote amide formation with the free acids such that they react with the acid in situ to form a reactive acid derivative include, in particular, alkylcarbodiimides, carbonyldiimidazole and N-lower alkyl-2-halopyridinium salts such as N-methyl-2-chloropyridinium iodide. The reaction in the presence of a coupling reagent can advantageously be carried out in an inert organic solvent, for example a halogenated hydrocarbon and/or an aromatic hydrocarbon, optionally in the presence of an acid-binding amine.

The compounds of formula I can be isolated from the reaction mixture in a known manner and purified. Acid addition salts can be converted in the customary manner to the free bases and these can be converted in a known manner, if desired, to pharmaceutically acceptable acid addition salts.

If the substituents $R^2$ and $R^3$ in the compounds of formula I are different, the compounds will contain an asymmetric center and can exist in two optically active forms or as a racemate. The present invention includes both the racemic mixtures and the optical isomers of such compounds of formula I. The optically active compounds can be obtained from the racemic mixtures in a known manner by conventional separation processes, e.g. by chromatographic separation on chiral separating materials or fractional crystallization of suitable salts using optically active acids. Enantiomerically pure compounds can also be prepared by synthesis from corresponding enantiomerically pure starting compounds of formula II.

The starting compounds of formula II are disclosed in U.S. Pat. No. 4,906,640 and/or can be prepared in a known manner by the methods described in U.S. Pat. No. 4,906,640 or by methods analogous to the methods described in this specification.

The starting compounds of formula III are known or can be prepared in a known manner. For example, aromatic compounds corresponding to the general formula IX

   IX in which $R^{4'''}$ and $R^5$ have the above meanings, can be converted to corresponding substituted benzenesulfochlorides of formula III in a known manner by reaction with chlorosulfonic acid and/or sulfonyl chloride.

The starting compounds of formula IV can be obtained by reacting compounds of formula II with sulfonic acid derivatives of the general formula VIII

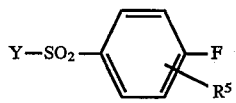   VIII in which Y and $R^5$ have the above meanings. The reaction can be carried out under the conditions described above for reacting compounds of formula II with compounds of formula Compounds of formula VI are novel compounds which are useful intermediates for preparing pharmacologically active compounds, for example compounds of formula Id. The compounds of formula VI can be obtained by a process in which the acyl group $R^{8'}$—CO— is hydrolytically removed from corresponding compounds of formula I in which $R^4$ is an acylamino radical $R^{8'}$—CO—NH— in which $R^{8'}$ has the above meaning. The hydrolysis can be carried out in a known manner under acidic or alkaline conditions.

It has now surprisingly been found that the compounds of formula I used according to the invention and their physiologically acceptable acid addition salts have antiarrhythmic effects. In particular, they exhibit class III antiarrhythmic properties and cause a prolongation of the effective refractory period in the heart, which leads to a prolongation of the QT interval in the ECG. The compounds have a favorable activity profile with good tolerability, a long duration of action and such a high selectivity of the antiarrhythmic action with respect to bradycardic and hypotensive properties that in the antiarrhythmically active dose range a therapeutically undesired effect on the heart rate and/or the blood pressure does not occur. The compounds are distinguished in that the antiarrhythmic activity is particularly highly pronounced under tachycardiac conditions.

The antiarrhythmic activity of the compounds can be demonstrated in standard pharmacological test methods.

Description of the pharmacological test methods.

1. Determination of the minimum toxic dose.

Male mice weighing 20 to 25 g were administered maximum doses of 300 mg/kg of the test substance p.o. The animals were observed carefully for toxicity symptoms for 3 hours. All symptoms and instances of death over a period of 72 hours after administration were additionally recorded. Concomitant symptoms were likewise observed and recorded. If death or severe toxic symptoms was observed, increasingly lower doses were administered to other mice until toxic symptoms no longer occurred. The lowest dose which caused death or severe toxic symptoms is indicated in the following Table A as the minimum toxic dose. The Example numbers given in Table A refer to the subsequent Preparation Examples.

TABLE A

| Test substance Example No. | Minimum toxic dose mg/kg mouse p.o. |
| --- | --- |
| 1 | >300 |
| 2 | >300 |
| 6 | >300 |
| 15 | >300 |
| 20 | >300 |
| 21 | >300 |
| 22 | >300 |
| 24 | >300 |
| 47 | >300 |

2. In vivo investigation of antiarrhythmic properties under tachycardiac conditions in anaesthetized guinea-pigs.

The effects of the substances on the effective refractory period (=ERP) and the blood pressure when administered i.v. at increased heart rate were investigated on anaesthetized guinea-pigs. A bipolar stimulation catheter was inserted into the right ventricle of the animals via a jugular vein under full anesthesia. The heart rate of the animals was maintained at about 150% of their normal heart rate via this by means of electrical stimulation during the entire investigation. A cannula for i.v. administration of the test substances was inserted in the other jugular vein. During the investigation, the systolic and the diastolic arterial blood pressure (=SAP and DAP) were measured in a carotid artery via a pressure gauge (Statham pressure transducer). The test substances were administered i.v. in increasing doses (cumulatively). Before administration of the first dose and in each case 8 minutes after administration of each dose, the ERP was determined by means of a double pulse protocol. The dose at which a prolongation of the ERP to 115% of the starting value was achieved was considered as the effective dose (=ERP-$ED_{115}$). Effective doses for a hypotensive effect were considered as that dose at which the SAP was decreased to 85% of its starting value (=SAP-$ED_{85}$), and the dose at which the DAP was decreased to 85% of its starting value (=DAP-$ED_{85}$).

The results obtained using the method described above are listed in the following Table B. The Example numbers given in Table B for the test substances refer to the subsequent Preparation Examples.

TABLE B

| Example No. | Antiarrhythmic activity ERP-$ED_{115}$ in μmole/kg i.v. | Blood pressure decrease $ED_{85}$ in μmole/kg i.v. | |
| --- | --- | --- | --- |
| | | DAP | SAP |
| 1 | 1 | 10 | 7 |
| 3 | 8 | >32 | >32 |
| 6 | 7 | >10 | >10 |
| 41 | 1 | >10 | >10 |
| 48 | 8 | — | — |

The activity of the test substances in prolonging the refractory period can also be confirmed in in vitro tests by determining the functional refractory period on the isolated papillary muscle of the right heart chamber of guinea-pigs.

The foregoing test results show that the compounds of formula I have antiarrhythmic effects and clearly prolong the effective refractory period of the heart muscle and that an effective hypotensive action of the substances first occurs at doses which are significantly higher than the doses effective for prolongation of the refractory period.

Due to their activity profile described above, the compounds are suitable for suppressing tachycardiac cardiac arrhythmias (extrasystoles, ventricular flutters and fibrillations) and can be used for the prophylaxis and treatment of cardiac arrhythmias in humans and other large mammals. In particular, the substances are suitable for preventing the occurrence of tachyarrhythmias, i.e. arrhythmias which are associated with an increase in the heart rate.

The doses to be used may differ from individual to individual and naturally vary depending on the type of condition to be treated, the substance used and the form of administration. In general, however, pharmaceutical dosage forms containing 0.5 to 100 mg of active agent, in particular 1 to 25 mg, per individual dose are suitable for administrations to larger mammals, in particular humans.

As medicines, the compounds of formula I can be combined with customary pharmaceutical auxiliaries in pharmaceutical preparations such as e.g. tablets, capsules, suppositories or solutions. These pharmaceutical preparations can be prepared by known methods using conventional solid or liquid vehicles such as e.g. lactose, starch or talc or liquid paraffins and/or using customary pharmaceutical adjuvants, for example tablet disintegrating agents, solubilizers or preservatives.

The following Examples are intended to illustrate the invention in further detail without restricting its scope.

EXAMPLE 1

7-(n-Butyl)-3-[(4-cyanophenyl)sulfonyl]-9,9-dimethyl-3,7-diazabicyclo[3.3.1]nonane.

A solution of 2.5 g of 4-cyanobenzenesulfonyl chloride in 20 ml of dichloromethane was added dropwise with ice-cooling to a solution of 2.37 g of 7-(n-butyl)-9,9-dimethyl-3,7-diazabicyclo[3.3.1]nonane in 30 ml of dichloromethane. The ice-cooling was then removed, and the reaction mixture was stirred at room temperature for one hour. The hydrochloride of the title compound was thereupon deposited as a white precipitate. The crystals were filtered out with suction and dried at 60° C. in a vacuum drying oven. 2.5 g of 7-(n-butyl)-3-[(4-cyanophenyl)sulfonyl]-9,9-dimethyl-3,7-diazabicyclo[3.3.1]nonane hydrochloride having a melting point of 98° to 99° C. were obtained.

EXAMPLE 2

7-(n-Butyl)-3-[(4-acetylaminophenyl)sulfonyl]-9,9-dimethyl-3,7-diazabicyclo[3.3.1]nonane.

A solution of 43.7 g of 4-acetamidosulfonyl chloride in 100 ml of dichloromethane was added dropwise with ice-cooling to a solution of 39.3 g of 7-(n-butyl)-9,9-dimethyl-3,7-diazabicyclo[3.3.1]nonane and 29 ml of triethylamine in 700 ml of dichloromethane. The reaction mixture was stirred at room temperature for a further 2 hours. The reaction mixture was then worked up by adding water and extracting the mixture twice with dichloromethane. The combined dichloromethane phases were dried with magnesium sulfate and concentrated. 42.4 g of 7-(n-butyl)-3-[(4-acetylaminophenyl)sulfonyl]-9,9-dimethyl-3,7-diazabicyclo[3.3.1]nonane were obtained as a residue.

2.9 g of the title base were dissolved in 20 ml of ethyl acetate. A solution of 1.1 g of tartaric acid in 20 ml of acetone was added to the solution with ice-cooling. The hydrogen tartrate of the title compound thereupon precipitated in crystalline form. The crystals were filtered out with suction and dried at 50° C. in a vacuum drying oven. 3.6 g of monohydrogen tartrate of the title compound having a melting point of 130° C. were obtained.

EXAMPLE 3

7-(n-Butyl)-3-[(4-(imidazol-1-yl)phenyl)-sulfonyl]-9,9-dimethyl-3,7-diazabicyclo[3.3.1]nonane.

A) A solution of 7.2 g of 4-fluorobenzenesulfonyl chloride in 10 ml of dichloromethane was added dropwise with ice-cooling to a solution of 7.8 g of 7-(n-butyl)-9,9-dimethyl-3,7-diazabicyclo[3.3.1]nonane in 40 ml of dichloromethane. The ice-cooling was then removed, and the reaction mixture was stirred at room temperature for 1 hour. The reaction mixture was worked up by adding aqueous sodium bicarbonate solution and extracting twice with dichloromethane. The combined dichloromethane extracts were dried with magnesium sulfate and concentrated. 12.9 g of 7-(n-butyl)-3-[(4-fluorophenyl)sulfonyl]-9,9-dimethyl-3,7-diazabicyclo[3.3.1]nonane were obtained.

B) 12.9 g of the product obtained above, 5.8 g of potassium carbonate and 2.4 g of imidazole were heated at 120° C. for 10 hours in 200 ml of dimethyl sulfoxide. The reaction mixture was then cooled, the potassium carbonate was filtered out, and the filtrate was concentrated. The residue which remained was treated with aqueous sodium hydroxide solution and extracted twice with dichloromethane. The combined dichloromethane extracts were dried with magnesium sulfate and concentrated. The crude title compound which remained as an oily residue was purified by chromatography on alumina using ethyl acetate as the eluent. 4.2 g of 7-(n-butyl)-3-[(4-imidazol-1-yl)phenyl)sulfonyl]-9,9-dimethyl-3,7-diazabicyclo[3.3.1]nonane having a melting point of 148° to 150° C. were obtained.

EXAMPLE 4

7-(n-Butyl)-3-[(4-(4-cyanobenzoylamino)phenyl)-sulfonyl]-9,9-dimethyl-3,7-diazabicyclo[3.3.1]nonane.

A) 5.1 g of 7-(n-Butyl)-3-[(4-acetylaminophenyl)-sulfonyl]-9,9-dimethyl-3,7-diazabicyclo[3.3.1]nonane (for preparation see Example 2) and 1.5 g of potassium hydroxide were refluxed for 6 hours in 100 ml of ethanol. The reaction mixture was then cooled, water was added, and the mixture was extracted twice with diethyl ether. The combined ether extracts were dried with magnesium sulfate and concentrated. 4.0 g of 7-(n-butyl)-3-[(4-aminophenyl)-sulfonyl]-9,9-dimethyl-3,7-diazabicyclo[3.3.]nonane were obtained, which were employed in the following reaction step without further purification.

B) 1.4 g of the product obtained above and 0.63 g of 4-cyanobenzoyl chloride were dissolved in 20 ml of dichloromethane. The reaction mixture was allowed to react at room temperature for 1 hour. The reaction mixture was worked up by rendering it alkaline by addition of aqueous sodium hydroxide solution. The aqueous phase was then separated and extracted twice with dichloromethane. The combined dichloromethane phases were dried with magnesium sulfate and concentrated. The crude title compound obtained as a crystalline residue was recrystallized from diethyl ether, and the resulting crystals were dried at 60° C. in a vacuum drying oven. 1.3 g of 7-(n-butyl)-3-[(4-(4-cyano-benzoyl-amino)phenyl)sulfonyl]-9,9-dimethyl-3,7-diaza-bicyclo[3.3.1]-nonane having a melting point of 145° C. were obtained.

The compounds of formula I listed in the following Table were also be prepared by the processes described in the foregoing Examples.

The following abbreviations are used in the table:

n = normal i = iso

Cyp = cyclopropyl

Cyh = cyclohexyl

HCl = hydrochloride

HTa = hydrogen tartrate

HMa = hydrogen malonate

| Example No. | $R^1$ | $R^2$ | $R^3$ | $R^4$ | $R^5$ | Salt | Melting Point (°C.) |
|---|---|---|---|---|---|---|---|
| 5 | n-$C_4H_9$— | $CH_3$— | $CH_3$— | 4-NH—CO—$CH_3$ | 3-F | 1 HTa | amorphous |
| 6 | n-$C_4H_9$— | $CH_3$— | $CH_3$— | 4-CO—$OCH_3$ | H | 1 HCl | 117–118 |
| 7 | n-$C_4H_9$— | n-$C_3H_7$— | $CH_3$— | 4-CN | H | base | 113–115 |
| 8 | n-$C_4H_9$— | n-$C_3H_7$— | $CH_3$— | 4-NH—$SO_2$—$CH_3$ | H | 1 HCl | 219 |
| 9 | n-$C_4H_9$— | n-$C_3H_7$— | $CH_3$— | 4-NH—CO—$CH_3$ | H | 1 HCl | amorphous |
| 10 | n-$C_4H_9$— | n-$C_3H_7$— | $CH_3$— | 4-imidazol-1-yl | H | base | 168–170 |
| 11 | n-$C_6H_{13}$— | n-$C_3H_7$ | $CH_3$— | 4-CN | H | 1.3 HCl | 103–106 |
| 12 | n-$C_4H_9$— | $CH_3$— | $CH_3$— | 2-CO—$OCH_3$ | H | 1.5 HTa | amorphous |
| 13 | $(CH_3)_2$—CH— | $CH_3$— | $CH_3$— | 4-CN | H | base | 129–130 |
| 14 | $(CH_3)_2$—CH— | $CH_3$— | $CH_3$— | 4-CO—$OCH_3$ | H | 1 HCl | 193 |
| 15 | $(CH_3)_2$—CH— | $CH_3$— | $CH_3$— | 4-imidazol-1-yl | H | base | 194 |
| 16 | n-$C_4H_9$— | n-$C_4H_9$— | n-$C_3H_7$— | 4-CN | H | base | 117–118 |
| 17 | n-$C_4H_9$— | n-$C_4H_9$— | n-$C_3H_7$— | 4-NH—CO—$CH_3$ | H | base | 156–159 |
| 18 | n-$C_4H_9$— | n-$C_4H_9$— | n-$C_3H_7$— | 4-NH—$SO_2$—$CH_3$ | H | 1 HCl | 239 |

-continued

| Example No. | $R^1$ | $R^2$ | $R^3$ | $R^4$ | $R^5$ | Salt | Melting Point (°C.) |
|---|---|---|---|---|---|---|---|
| 19 | n-$C_4H_9$— | $CH_3$— | $CH_3$— | 4-NH—$SO_2$—$CH_3$ | H | 0.9 HCl | 230–232 |
| 20 | n-$C_6H_{13}$— | $CH_3$— | $CH_3$— | 4-NH—$SO_2$—$CH_3$ | H | 1 HCl | 210–211 |
| 21 | n-$C_6H_{13}$— | $CH_3$— | $CH_3$— | 4-CN | H | 1 HMa | 146 |
| 22 | n-$C_6H_{13}$— | $CH_3$— | $CH_3$— | 4-NH—CO—$CH_3$ | H | 1 HCl | 152 |
| 23 | n-$C_6H_{13}$— | $CH_3$— | $CH_3$— | 4-imidazol-1-yl | H | base | 112–113 |
| 24 | n-$C_4H_9$— | $CH_3$— | $CH_3$— | 4-NH—CO-(4-$NO_2$-phenyl) | H | 1 HTa | amorphous |
| 25 | n-$C_4H_9$— | $CH_3$— | $CH_3$— | 4-NH—CO-phenyl | H | 1 HTa | 191–192 |
| 26 | n-$C_4H_9$— | $CH_3$— | $CH_3$— | 4-NH—CO-(4-Cl-phenyl) | H | 1.4 HTa | 125 |
| 27 | n-$C_4H_9$— | $CH_3$— | $CH_3$— | 4-NH—CO-(4-Br-phenyl) | H | 1.4 HCl | 236–238 |
| 28 | n-$C_4H_9$— | $CH_3$— | $CH_3$— | 4-NH—CO-(4-$CH_3SO_2$-phenyl) | H | 1.25 HTa | 163 |
| 29 | i-$C_4H_9$— | —$(CH_2)_5$— | | 4-CN | H | base | 140–143 |
| 30 | i-$C_4H_9$— | —$(CH_2)_5$— | | 4-CO—$OCH_3$ | H | 1 HCl | 95–98 |
| 31 | i-$C_4H_9$— | —$(CH_2)_5$— | | 4-imidazol-1-yl | H | base | 196–200 |
| 32 | n-$C_4H_9$— | n-$C_4H_9$— | n-$C_4H_9$— | 4-CN | H | base | 105–110 |
| 33 | Cyp-$CH_2$— | —$(CH_2)_4$— | | 4-CN | H | 1 HCl | 79–80 |
| 34 | $CH_3$— | —$(CH_2)_5$— | | 4-CN | H | base | 182 |
| 35 | n-$C_4H_9$— | $CH_3$— | $CH_3$— | 3-$NO_2$ | H | 1 HCl | 130–132 |
| 36 | n-$C_4H_9$— | n-$C_3H_7$— | $CH_3$— | 4-$NO_2$ | H | base | 135 |
| 37 | n-$C_4H_9$— | —$(CH_2)_4$— | | 4-Cl | H | 1 HCl | 92–97 |
| 38 | n-$C_4H_9$— | $CH_3$— | $CH_3$— | 4-Cl | H | 1 HCl | 132–137 |
| 39 | n-$C_4H_9$— | $CH_3$— | $CH_3$— | H | H | 1 HTa | amorphous |
| 40 | n-$C_4H_9$— | $CH_3$— | $CH_3$— | 2-$NO_2$ | H | 1 HTa | 173 |
| 41 | n-$C_4H_9$— | $CH_3$— | $CH_3$— | 4-$NO_2$ | H | 1 HMa | 160–162 |
| 42 | n-$C_4H_9$— | $CH_3$— | $CH_3$— | 4-F | H | 1 HTa | amorphous |
| 43 | n-$C_4H_9$— | $CH_3$— | $CH_3$— | 4-Br | H | 1 HCl | 177–178 |
| 44 | n-$C_4H_9$— | $CH_3$— | $CH_3$— | 3-Cl | 4-Cl | 1 HCl | 170–173 |
| 45 | n-$C_4H_9$— | $CH_3$— | $CH_3$— | 3-Cl | 4-F | 1 HCl | 165 |
| 46 | n-$C_4H_9$— | $CH_3$— | $CH_3$— | 4-$CF_3$ | H | 2 HTa | amorphous |
| 47 | n-$C_4H_9$— | —$(CH_2)_4$— | | 4-$NO_2$ | H | 1 HCl | 107 |
| 48 | $(CH_3)_2CH$— | —$(CH_2)_4$— | | 4-$NO_2$ | H | 1 HMa | 140 |
| 49 | n-$C_4H_9$— | n-$C_4H_9$— | n-$C_3H_7$— | 4-$NO_2$ | H | 1 HMa | 141–143 |
| 50 | n-$C_4H_9$— | n-$C_3H_7$— | n-$C_3H_7$— | 4-Br | H | 1 HCl | 157–158 |
| 51 | Cyh-$CH_2$— | —$(CH_2)_5$— | | 4-Br | H | base | 143–145 |
| 52 | n-$C_6H_{13}$— | $CH_3$— | $CH_3$— | 4-F | H | 1.4 HTa | amorphous |
| 53 | i-$C_4H_9$— | —$(CH_2)_5$— | | 4-$NO_2$ | H | base | 157–159 |
| 54 | n-$C_4H_9$— | —$(CH_2)_5$— | | 4-Br | H | 1 HCl | 211 |
| 55 | Cyh-$CH_2$— | $CH_3$— | $CH_3$— | 3-Cl | H | 1 HTa | amorphous |
| 56 | n-$C_4H_9$— | n-$C_3H_7$— | n-$C_3H_7$— | 3-Cl | H | base | 45–48 |
| 57 | n-$C_4H_9$— | $CH_3$— | $CH_3$— | 2-Cl | H | 1 HTa | amorphous |
| 58 | n-$C_4H_9$— | $CH_3$— | $CH_3$— | 3-Cl | H | 1 HTa | 102 |
| 59 | n-$C_4H_9$— | $CH_3$— | $CH_3$— | 2-Cl | 5-Cl | 1 HTa | amorphous |
| 60 | n-$C_4H_9$— | $CH_3$— | $CH_3$— | 3-Cl | 5-Cl | 0.8 HCl | 194 |
| 61 | $C_2H_5$— | $CH_3$— | $CH_3$— | 3-Cl | H | 1.4 HTa | 100 |
| 62 | n-$C_5H_{11}$— | $CH_3$— | $CH_3$— | 3-Cl | H | 1 HTa | 159–160 |
| 63 | n-$C_5H_{11}$— | $CH_3$— | $CH_3$— | 4-Br | H | 1 HCl | 218–222 |
| 64 | n-$C_4H_9$— | $CH_3$— | $CH_3$— | 4-I | H | 1 HCl | 222–227 |
| 65 | n-$C_4H_9$— | $CH_3$— | $CH_3$— | 2-$CF_3$ | H | base | 63 |
| 66 | n-$C_4H_9$— | $CH_3$— | $CH_3$— | 3-$CF_3$ | H | 1 HCl | 114 |
| 67 | n-$C_4H_9$— | $CH_3$— | $CH_3$— | 3-$NO_2$ | 4-Cl | base | 73–75 |
| 68 | $(CH_3)_2CH$— | $CH_3$— | $CH_3$— | 4-Br | H | base | 140 |
| 69 | $(CH_3)_2CH$— | $CH_3$— | $CH_3$— | 3-Cl | H | base | 130 |
| 70 | Cyh-$CH_2$— | $CH_3$— | $CH_3$— | 4-Br | H | 1 HTa | amorphous |
| 71 | $(CH_3)_2CH$— | —$(CH_2)_5$— | | 3-Cl | H | base | 134–135 |
| 72 | n-$C_4H_9$— | —$(CH_2)_5$— | | 3-Cl | H | 1 HTa | 202 |
| 73 | $(CH_3)_2CH$— | —$(CH_2)_5$— | | 4-Br | H | base | 135 |
| 74 | n-$C_4H_9$— | n-$C_3H_7$— | n-$C_3H_7$— | -Cl | 4-Cl | base | 96 |

EXAMPLE I

Tablets containing 7-(n-butyl)-3-[(4-cyano-phenyl)sulfonyl]-9,9-dimethyl-3,7-diazabicyclo[3.3.1]nonane hydrochloride.

Tablets were prepared having the following composition per tablet:

| | |
|---|---|
| 7-(n-Butyl)-3-[(4-cyanophenyl)sulfonyl]-9,9-dimethyl-3,7-diazabicyclo[3.3.1]nonane hydrochloride | 20 mg |
| Maize starch | 60 mg |
| Lactose | 135 mg |
| Gelatine (as 10% strength solution) | 6 mg |

The active compound, the maize starch and the lactose were thickened using the 10% strength gelatine solution. The paste was comminuted, and the resulting granules were transferred to a suitable sheet and dried at 45° C. The dried granules were passed through a mill mixed with the following further adjuvants in a mixer:

| | |
|---|---|
| Talc | 5 mg |
| Magnesium stearate | 5 mg |
| Maize starch | 9 mg | and then pressed to give 240 mg tablets.

The foregoing description and examples have been set forth merely to illustrate the invention and are not intended to be limiting. Since modifications of the disclosed embodiments incorporating the spirit and substance of the invention may occur to persons skilled in the art, the invention should

What is claimed is:

1. A compound corresponding to the formula Ia

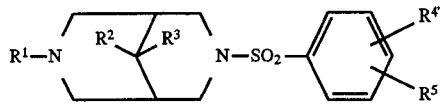

wherein

R$^1$ is an alkyl group having 1–6 carbon atoms or a cycloalkylalkyl group having 4–7 carbon atoms, R$^2$ and R$^3$ are each independently lower alkyl or together form an alkylene chain having 3–6 carbon atoms, R$^{4'}$ is cyano, an R$^6$—O—CO— group in which R$^6$ is lower alkyl, an R$^7$—SO$_2$—NH— group in which R$^7$ is lower alkyl, or an R$^8$—CO—NH— group in which R$^8$ is lower alkyl or a phenyl group which is optionally substituted by halogen, cyano nitro or an R$^9$—SO$_2$— radical in which R$^9$ is lower alkyl, or an imidazolyl radical located in position 4 of the phenyl ring, and R$^5$ is hydrogen or halogen;

or a physiologically acceptable acid addition salt thereof.

2. A pharmaceutical composition comprising an effective heart rhythm affecting amount of a compound according to claim 1, and at least one pharmaceutical carrier or adjuvant.

* * * * *